US006432418B1

(12) United States Patent
Dubief et al.

(10) Patent No.: US 6,432,418 B1
(45) Date of Patent: *Aug. 13, 2002

(54) COSMETIC COMPOSITION INCLUDING AT LEAST ONE SILICONE-GRAFTED POLYMER AND AT LEAST ONE POLYSILOXANE-POLYOXYALKYLENE LINEAR BLOCK COPOLYMER

(75) Inventors: Claude Dubief, Le Chesnay; Christine Dupuis; Daniele Cauwet-Martin, both of Paris, all of (FR)

(73) Assignee: L'Oreal, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/983,305

(22) PCT Filed: Sep. 16, 1996

(86) PCT No.: PCT/FR96/01433

§ 371 (c)(1),
(2), (4) Date: Dec. 30, 1997

(87) PCT Pub. No.: WO97/12593

PCT Pub. Date: Apr. 10, 1997

(30) Foreign Application Priority Data

Sep. 29, 1995 (FR) .............................. 95 11479

(51) Int. Cl.$^7$ ................................. A61K 7/00
(52) U.S. Cl. ................. 424/401; 424/78.08; 424/78.17; 424/78.21; 424/78.31; 424/70.12; 424/70.16
(58) Field of Search ........................... 424/78.08, 78.17, 424/78.21, 78.31, 70.12, 70.16, 401

(56) References Cited

U.S. PATENT DOCUMENTS 5,362,485 A  11/1994 Hayama et al. ............... 424/70
5,618,524 A  4/1997 Bolich, Jr. et al. ....... 424/70.12
5,660,819 A * 8/1997 Tsubaki et al. ............ 424/70.1

FOREIGN PATENT DOCUMENTS

| EP | 0 125 779 | 11/1984 |
| EP | 0 412 704 | 2/1991 |
| EP | 0 412 707 | 2/1991 |
| EP | 0 492 657 | 7/1992 |
| EP | 0 582 152 | 2/1994 |
| WO | WO 93/23009 | 11/1993 |
| WO | WO 93/23446 | 11/1993 |
| WO | WO 95/03776 | 2/1995 |

OTHER PUBLICATIONS

English language abstract of JP 04–211,605, Aug. 3, 1992.
English Language Derwent Abstract of EP 0 635 258.
English Language Derwent Abstract of EP 0 643 961.
English Language Derwent Abstract of FR 2 709 995.

* cited by examiner

Primary Examiner—Jose' G. Dees
Assistant Examiner—Michael A. Williamson
(74) Attorney, Agent, or Firm—Finnegan, Henderson, Farabow, Garrett & Dunner, L.L.P.

(57) ABSTRACT

A cosmetic or dermatological composition for treating keratinous material, particularly human hair, including a cosmetically or dermatologically acceptable medium containing at least one silicone-grafted polymer with a polysiloxane portion and a portion consisting of a non-silicone organic chain, wherein one of the two portions constitutes the main polymeric chain while the other is grafted onto said main chain, and at least one copolymer with a polysiloxane-polyoxyalkylene linear block as the repetitive units, as well as the uses thereof, are disclosed. Such compositions are particularly suitable for use as rinsable or non-rinsable products for washing and conditioning hair, hair setting or hair styling.

67 Claims, No Drawings

COSMETIC COMPOSITION INCLUDING AT LEAST ONE SILICONE-GRAFTED POLYMER AND AT LEAST ONE POLYSILOXANE-POLYOXYALKYLENE LINEAR BLOCK COPOLYMER

The present invention relates to a cosmetic or dermatological composition for treating keratin substances, in particular human hair, this composition comprising at least one grafted silicone polymer and at least one copolymer having a linear polysiloxane/polyoxyalkylene block as repeating units.

Grafted silicone polymers are known in the prior art, such as those described in patent applications EP-A-0,412,704, EP-A-0,412,707, EP-A-0,640,105, WO 95/00578, EP-A-0,582,152 and WO 93/23009. These polymers are used in hair care for their styling properties. However, when these polymers are used, the fixing power, the hold of the hairstyle and the feel of the hair are still unsatisfactory.

The expression fixing power of the composition will be understood to denote the ability of this composition to give the hair cohesion such that the initial shape of the hairstyle is held.

Silicones are known which possess grafted polyoxyalkylene chains, also known as dimethicone copolyol according to the CTFA nomenclature. The Applicant has observed that these silicones lower the fixing power of compositions for holding the hairstyle.

The Applicant has discovered, surprisingly, that by combining at least one grafted silicone polymer with at least one copolymer having a linear polysiloxane/polyoxyalkylene block as repeating units, the fixing power of the compositions and the feel of the hair are substantially superior to those obtained with the grafted silicone polymer used alone.

The composition according to the invention is thus essentially characterized in that it contains, in a cosmetically or dermatologically acceptable medium, at least one grafted silicone polymer comprising a polysiloxane portion and a portion consisting of a non-silicone organic chain, one of the two portions constituting the main chain of the polymer, the other being grafted onto the said main chain, and at least one copolymer having a linear polysiloxane/polyoxyalkylene block as repeating units.

The grafted silicone polymers according to the invention are preferably chosen from polymers having a non-silicone organic skeleton grafted with monomers containing a polysiloxane, polymers having a polysiloxane skeleton grafted with non-silicone organic monomers and mixtures thereof.

In the following text, in accordance with what is generally accepted, the term silicone or polysiloxane is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bonding ≡Si—O—Si≡), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy radicals or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

In the following text, in accordance with what is generally accepted, the expression "polysiloxane macromer" is understood to refer to any monomer containing a polysiloxane-type polymer chain in its structure.

The polymers containing a non-silicone organic skeleton grafted with monomers containing a polysiloxane, in accordance with the present invention, consist of an organic main chain formed from organic monomers containing no silicone, on which is grafted, inside the said chain and optionally on at least one of its ends, at least one polysiloxane macromer.

The non-silicone organic monomers constituting the main chain of the grafted silicone polymer can be chosen from monomers containing ethylenic unsaturation which are polymerizable via a radical route, monomers which are polymerizable by polycondensation, such as those forming polyamides, polyesters or polyurethanes, and monomers which involve ring opening, such as those of the oxazoline or caprolactone type.

The polymers containing a non-silicone organic skeleton grafted with monomers containing a polysiloxane, in accordance with the present invention, can be obtained according to any means known to those skilled in the art, in particular by reaction between (i) a starting polysiloxane macromer which is correctly functionalized on the polysiloxane chain and (ii) one or more non-silicone organic compounds, themselves correctly functionalized with a function which is capable of reacting with the functional group(s) borne by the said silicone, forming a covalent bond; a classic example of such a reaction is the radical reaction between a vinyl group borne on one of the ends of the silicone with a double bond of a monomer containing ethylenic unsaturation in the main chain.

The polymers containing a non-silicone organic skeleton grafted with monomers containing a polysiloxane, in accordance with the invention, are more preferably chosen from those described in U.S. Pat. Nos. 4,693,935, 4,728,571 and 4,972,037 and patent applications EP-A-0,412,704, EP-A-0,412,707, EP-A-0,640,105 and WO 95/00578. These are copolymers obtained by radical polymerization starting with monomers containing ethylenic unsaturation and silicone macromers having a terminal vinyl group, or alternatively copolymers obtained by reaction of a polyolefin comprising functionalized groups and a polysiloxane macromer having a terminal function which is reacted with the said functionalized groups.

One particular family of grafted silicone polymers which is suitable for carrying out the present invention consists of silicone grafted copolymers comprising:
   a) from 0 to 98% by weight of at least one lipophilic monomer (A) of low lipophilic polarity containing ethylenic unsaturation, which is polymerizable via a radical route;
   b) from 0 to 98% by weight of at least one polar hydrophilic monomer (B) containing ethylenic unsaturation, which is copolymerizable with the (A)-type monomer(s);

c) from 0.01 to 50% by weight of at least one polysiloxane macromer (C) of general formula:

$$X(Y)_nSi(R)_{3-m}Z_m \qquad (I)$$

where:
X denotes a vinyl group which is copolymerizable with the monomers (A) and (B);
Y denotes a divalent bonding group;
R denotes a hydrogen, a $C_1-C_6$ alkyl or alkoxy or a $C_6-C_{12}$ aryl;
Z denotes a monovalent polysiloxane unit having a number-average molecular weight of at least 500;
n is 0 or 1 and m is an integer ranging from 1 to 3;
the percentages being calculated relative to the total weight of the monomers (A), (B) and (C).

These polymers are described, along with processes for their preparation, in U.S. Pat. Nos. 4,693,935, 4,728,571 and 4,972,037 and in patent applications EP-A-0,412,704, EP-A-0,412,707 and EP-A-0,640,105. They have a number-average molecular weight preferably ranging from 10,000 to 2,000,000 and preferably a glass transition temperature Tg or a crystalline melting point Tm of at least −20° C.

As examples of lipophilic monomers (A), mention may be made of acrylic or methacrylic acid esters of $C_1-C_{18}$ alcohols; styrene; polystyrene macromers; vinyl acetate; vinyl propionate; a-methylstyrene; tert-butylstyrene; butadiene; cyclohexadiene; ethylene; propylene; vinyltoluene; acrylic or methacrylic acid esters of 1,1-dihydroperfluoroalkanols or of homologues thereof; acrylic or methacrylic acid esters of ω-hydridofluoroalkanols; acrylic or methacrylic acid esters of fluoroalkylsulphoamido alcohols; acrylic or methacrylic acid esters of fluoroalkyl alcohols; acrylic or methacrylic acid esters of fluoroether alcohols; or mixtures thereof. The preferred monomers (A) are chosen from the group consisting of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate and 2-(N-butylperfluorooctanesulphonamido)ethyl acrylate, and mixtures thereof.

As examples of polar monomers (B), mention may be made of acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and semiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam, or mixtures thereof. The preferred monomers (B) are chosen from the group consisting of acrylic acid, N,N-dimethylacrylamide, dimethylaminoethyl methacrylate, quaternized dimethylaminoethyl methacrylate and vinylpyrrolidone, and mixtures thereof.

The preferred polysiloxane macromers (C) of formula (I) are chosen from those corresponding to the general formula (II) below:

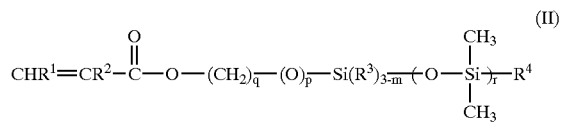

in which:
$R^1$ is hydrogen or —COOH (preferably hydrogen);
$R^2$ is hydrogen, methyl or —CH$_2$COOH (preferably methyl);
$R^3$ is $C_1-C_6$ alkyl, alkoxy, or alkylamino, $C_6-C_{12}$ aryl or hydroxyl (preferably methyl);
$R^4$ is $C_1-C_6$ alkyl, alkoxy or alkylamino, $C_6-C_{12}$ aryl or hydroxyl (preferably methyl);
q is an integer from 2 to 6 (preferably 3);
p is 0 or 1;
r is an integer from 5 to 700;
m is an integer from 1 to 3 (preferably 1).

The polysiloxane macromers of formula:

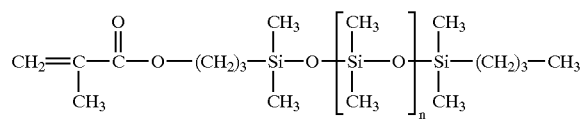

with n being an integer ranging from 5 to 700, are more particularly used.

One particular embodiment of the invention consists in using a copolymer which can be obtained by radical polymerization starting with the monomer mixture consisting of:
a) 60% by weight of tert-butyl acrylate;
b) 20% by weight of acrylic acid;
c) 20% by weight of silicone macromer of formula:

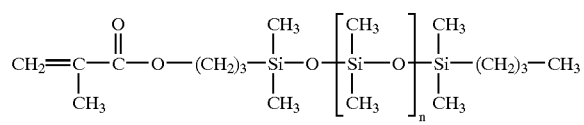

with n being an integer ranging from 5 to 700; the weight percentages being calculated relative to the total weight of the monomers.

Another particular embodiment of the invention consists in using a copolymer which can be obtained by radical polymerization starting with the monomer mixture consisting of:
a) 80% by weight of tert-butyl acrylate;
b) 20% by weight of silicone macromer of formula:

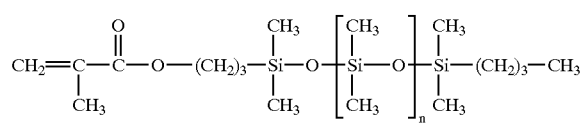

with n being an integer ranging from 5 to 700; the weight percentages being calculated relative to the total weight of the monomers.

Another particular family of grafted silicone polymers containing a non-silicone organic skeleton, which is suitable for carrying out the present invention, consists of silicone grafted copolymers which can be obtained by reactive extrusion of a polysiloxane macromer having a terminal reactive function, with a polyolefin-type polymer containing reactive groups which can react with the terminal function of the polysiloxane macromer in order to form a covalent bond allowing grafting of the silicone to the main chain of the polyolefin.

These polymers are described, along with a process for their preparation, in patent application WO 95/00578.

The reactive polyolefins are preferably chosen from polyethylenes or polymers of ethylene-derived monomers such as propylene, styrene, alkylstyrene, butylene, butadiene, (meth)acrylates, vinyl esters or equivalents, containing reactive functions which can react with the terminal function of the polysiloxane macromer. They are chosen more particularly from copolymers of ethylene or of ethylene derivatives and of monomers chosen from those containing a carboxylic function, such as (meth)acrylic acid; those containing an acid anhydride function such as maleic anhydride; those containing an acid chloride function such as (meth)acryloyl chloride; those containing an ester function such as (meth) acrylic acid esters; those containing an isocyanate function.

The silicone macromers are preferably chosen from polysiloxanes containing a functionalized group, at the end of the polysiloxane chain or close to the end of the said chain, chosen from the group consisting of alcohols, thiols, epoxy groups and primary and secondary amines, and more particularly from those corresponding to the general formula:

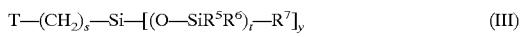

$$T-(CH_2)_s-Si-[(O-SiR^5R^6)_t-R^7]_y \quad (III)$$

in which T is chosen from the group consisting of $NH_2$, NHR', an epoxy, OH, or SH function; $R^5$, $R^6$, $R^7$ and R', independently denote a $C_1$–$C_6$ alkyl, phenyl, benzyl, $C_6$–$C_{12}$ alkylphenyl or hydrogen; s is a number from 2 to 100; t is a number from 0 to 1000 and y is a number from 1 to 3. They have a number-average molecular weight preferably ranging from 5000 to 300,000, more preferably from 8000 to 200,000 and more particularly from 9000 to 40,000.

According to the present invention, the grafted silicone polymer(s) containing a polysiloxane skeleton grafted with non-silicone organic monomers comprise a silicone (or polysiloxane ($\equiv$Si—O—)$_n$) main chain on which is grafted, inside the said chain as well as, optionally, on at least one of its ends, at least one organic group containing no silicone.

The polymers containing a polysiloxane skeleton grafted with non-silicone organic monomers, according to the invention, can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv$Si—H groups and vinyl groups $CH_2$=CH—, or alternatively the reaction between thio functional groups —SH with these same vinyl groups.

Examples of polymers with a polysiloxane skeleton grafted containing non-silicone organic monomers which are suitable for carrying out the present invention, as well as their specific mode of preparation, are described in particular in patent applications EP-A-0,582,152, WO 93/23009 and WO 95/03776, the teachings of which are included in, their entirety in the present description by way of non-limiting references.

According to a particularly preferred embodiment of the present invention, the silicone polymer containing a polysiloxane skeleton grafted with non-silicone organic monomers, which is used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one, and preferably several, functional groups capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical (homo) polymerization of at least one anionic monomer of unsaturated carboxylic acid type can, after reaction, be post-neutralized with a base (sodium hydroxide, aqueous ammonia, etc) in order to bring it into the form of a salt.

According to the present invention, the hydrophobic monomers containing ethylenic unsaturation are preferably chosen, alone or as a mixture, from acrylic acid esters of alkanols and/or methacrylic acid esters of alkanols. The alkanols are preferably $C_1$–$C_{18}$ and more particularly $C_1$–$C_{12}$. The preferred monomers are chosen from the group consisting of isooctyl (meth)acrylate, isononyl (meth) acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth) acrylate, tridecyl (meth)acrylate and stearyl (meth)acrylate, or mixtures thereof.

One family of silicone polymers containing a polysiloxane skeleton grafted with non-silicone organic monomers which is particularly suitable for carrying out the present invention consists of silicone polymers containing in their structure the unit of formula (IV) below:

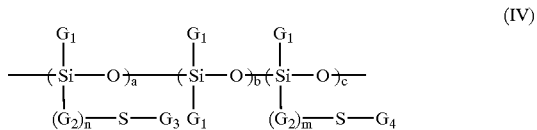

(IV)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (IV) above has at least one, and even more preferably all, of the following characteristics:

the radicals $G_1$ denote an alkyl radical, preferably the methyl radical;

n is non-zero and the radicals $G_2$ represent a divalent $C_1$–$C_3$ radical, preferably a propylene radical;

$G_3$ represents a polymeric radical resulting from the (homo)polymerization of at least one monomer of the carboxylic acid type containing ethylenic unsaturation, preferably acrylic acid and/or methacrylic acid;

G₄ represents a polymeric radical resulting from the (homo)polymerization of at least one monomer of the $C_1$–$C_{10}$ alkyl (meth)acrylate type, preferably isobutyl or methyl (meth)acrylate.

Examples of silicone polymers corresponding to formula (IV) are, in particular, polydimethylsiloxanes (PDMS) on which are grafted, via a thiopropylene-type connecting chain, mixed polymer units of the poly(meth)acrylic acid type and of the polymethyl (meth)acrylate type.

Other examples of silicone polymers corresponding to formula (IV) are, in particular, polydimethylsiloxanes (PDMS) on which are grafted, via a thiopropylene-type connecting chain, polymer units of the polyisobutyl (meth) acrylate type.

Preferably, the number-average molecular mass of the silicone polymers containing a polysiloxane skeleton grafted with non-silicone organic monomers, of the invention, ranges approximately from 10,000 to 1,000,000 and even more preferably approximately from 10,000 to 100,000.

The grafted silicone polymers in accordance with the invention are preferably used in an amount ranging from 0.01 to 20% by weight relative to the total weight of the composition. More preferably, this amount ranges from 0.1 to 15% by weight and even more particularly from 0.5 to 10% by weight.

The block copolymers having a linear polysiloxane/polyoxyalkylene block as repeating units, which are used in the context of the present invention, preferably have the following general formula:

$$([Y(R_2siO)_aR'_2SiYO][(C_nH_{2n}O)_b])_2 \quad (V)$$

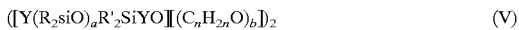

in which:
R and R', which may be identical or different, represent a monovalent hydrocarbon radical containing no aliphatic unsaturation,
n is an integer ranging from 2 to 4,
a is an integer greater than or equal to 5, preferably between 5 and 200 and even more particularly between 5 and 100,
b is an integer greater than or equal to 4, preferably between 4 and 200 and even more particularly between 5 and 100,
c is an integer greater than or equal to 4, preferably between 4 and 1000 and even more particularly between 5 and 300,
Y represents a divalent organic group which is linked to the adjacent silicon atom via a carbon-silicon bond and to a polyoxyalkylene block via an oxygen atom,
the average molecular weight of each siloxane block is between about 400 and about 10,000, that of each polyoxyalkylene block being between about 300 and about 10,000,
the siloxane blocks represent from about 10% to about 95% of the weight of the block copolymer,
the average molecular weight of the block copolymer being at least 3000 and preferably between 5000 and 1,000,000 and even more particularly between 10,000 and 200,000.

R and R' are preferably chosen from the group comprising alkyl radicals such as, for example, methyl, ethyl, propyl, butyl, pentyl, hexyl, octyl, decyl and dodecyl radicals, aryl radicals such as, for example, phenyl and naphthyl, aralkyl radicals such as, for example, benzyl and phenylethyl, and tolyl, xylyl and cyclohexyl radicals.

Y is preferably —R"—, —RH—CO—, —R"—NHCO—, —R"—NH—CO—NH—R'"—NHCO, —R"—OCONH—R'"—NHCO—, where R" is a divalent alkylene group such as, for example, ethylene, propylene or butylene and R'" is a divalent alkylene group or a divalent arylene group such as —$C_6H_4$—, —$C_6H_4$—$C_6H_4$—, —$C_6H_4$—$CH_2$—$C_6H_4$—, —$C_6H_4$—$C(CH_3)_2$—$C_6H_4$—.

Even more preferably, Y represents a divalent alkylene radical, more particularly the —$CH_2$—$CH_2$—$CH_2$-radical or the $C_4H_8$ radical.

The preparation of the block copolymers used in the context of the present invention is described in European patent application EP 0,492,657 A1, the teaching of which is included in the present description by way of reference.

The preferred linear polysiloxane/polyoxyalkylene block copolymers according to the invention are chosen from those of formula:

$$[C_4H_8O(C_nH_{2n}O)_b(C_mH_{2m}O)_d\text{—}C_4H_8\text{—}SiMe_2O(SiMe_2)_a \\ SiMe_2]_c \quad (VI)$$

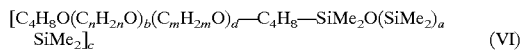

where Me represents methyl, n and m are integers ranging from 2 to 4, a is an integer greater than or equal to 4, preferably between 5 and 200, b and d are integers greater than or equal to 0, preferably between 4 and 200, b+d is greater than or equal to 4, preferably between 4 and 200, and c is a number greater than or equal to 4, preferably between 4 and 1000.

Among these copolymers, those having a repeating unit of formula:

$$[\text{—}(SiMe_2O)_xSiMe_2\text{—}C_4H_8O\text{—}(C_2H_4O)_y\text{—}(C_3H_6O)_z\text{—} \\ C_4H_8\text{—}] \quad (VII)$$

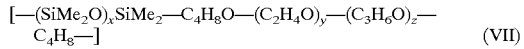

where x is a number between 5 and 15 (limits included), y is a number between 15 and 30 (limits included) and z is a number between 20 and 40 (limits included), are used more particularly.

Among these polymers, those whose siloxane/polyoxyalkylene weight ratio is about 20 and whose polyoxyethylene/polyoxypropylene weight ratio is about 65/35 are used more particularly.

It is also possible to choose polymers whose repeating unit is of formula (VI) and whose siloxane/polyoxyalkylene weight ratio is about 75 and whose polyoxyethylene/polyoxypropylene weight ratio is about 50/50, polymers whose siloxane/polyoxyalkylene weight ratio is about 35 and whose polyoxyethylene/polyoxypropylene weight ratio is about 100/0, and polymers whose siloxane/polyoxyalkylene weight ratio is about 30 and whose polyoxyethylene/polyoxypropylene weight ratio is about 0/100.

According to a particular embodiment of the invention, the block copolymer is chosen from the following copolymers:

[[(CH₃)₂SiO]₄₁(CH₃)₂SiCH₂CH(CH₃)CH₂ —O(C₂H₄O)₁₈—(C₃H₆O)₃₃CH₂CH(CH₃)CH₂]₁₆.₁
[[(CH₃)₂SiO]₃₁(CH₃)₂SiCH₂CH(CH₃)CH₂—O(C₂H₄O)₂₀—(C₃H₆O)₂₉CH₂CH(CH₃)CH₂]₁₃.₃
[[(CH₃)₂SiO]₉(CH₃)₂SiCH₂CH(CH₃)CH₂—O(C₂H₄O)₂₀—(C₃H₆O)₂₉CH₂CH(CH₃)CH₂]₂₆.₃
[[(CH₃)₂SiO]₁₆(CH₃)₂SiCH₂CH(CH₃)CH₂—O(C₂H₄O)₁₈—(C₃H₆O)₂₀CH₂CH(CH₃)CH₂]₂₁.₅
[[(CH₃)₂SiO]₉(CH₃)₂SiCH₂CH(CH₃)CH₂—O(C₂H₄O)₅—CH₂CH(CH₃)CH₂]₄.₈

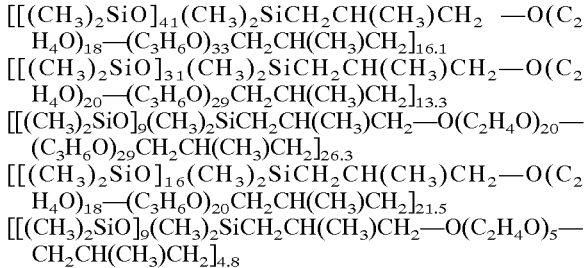

The linear block copolymer is preferably used in an amount of between 0.01 and 20% by weight relative to the total weight of the composition. More preferably, this amount is between 0.1 and 15% by weight and even more particularly between 0.5 and 10% by weight.

According to a preferred embodiment of the invention, the composition also contains a polymer, preferably a non-silicone anionic or amphoteric polymer, in solubilized form or in dispersed form.

The cosmetically or dermatologically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and ispropanol, polyalcohols such as diethylene glycol, glycol ethers, glycol alkyl ethers or diethylene glycol alkyl ethers.

The grafted silicone polymers according to the invention can be dissolved in the said cosmetically acceptable medium or used in the form of an aqueous dispersion of particles.

The composition of the invention can also contain at least one additive chosen from thickeners, fatty acid esters, fatty acid esters of glycerol, silicones, surfactants, fragrances, preserving agents, sunscreens, proteins, vitamins, plant, animal, mineral or synthetic oils or any other additive conventionally used in the cosmetic field.

These additives are present in the composition according to the invention in proportions which can range from 0 to 20% by weight relative to the total weight of the composition. The precise amount of each additive depends on its nature and is determined readily by those skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of a gel, a milk, a cream, a relatively thickened lotion or a mousse.

The compositions of the invention are used as rinse-out products or as leave-in products in particular to wash, care for, condition, maintain the style of or shape keratin substances such as the hair.

These compositions are more particularly styling products such as hairsetting lotions, blow-drying lotions, fixing compositions (lacquers) and styling compositions. The lotions can be packaged in various forms, in particular in vapourizers, pump-dispenser bottles or in aerosol containers in order to ensure application of the composition in vapourized form or in the form of a mousse. Such packaging forms are indicated, for example, when it is desired to obtain a spray, a lacquer or a mousse for fixing or treating the hair.

The compositions can also be shampoos, rinse-out or leave-in compositions, to be applied before or after shampooing, dyeing, bleaching, permanent-waving or straightening the hair.

When the composition according to the invention is packaged in aerosol form in order to obtain a lacquer or an aerosol mousse, it comprises at least one propellant which can be chosen from volatile hydrocarbons such as n-butane, propane, isobutane, pentane, a chloro and/or fluoro hydrocarbon, and mixtures thereof. Carbon dioxide, nitrous oxide, dimethyl ether, nitrogen or air, which is compressed, and mixtures thereof, can also be used as propellant.

Another subject of the invention is a process for treating keratin substances such as the hair, which consists in applying a composition as defined above to the hair and then optionally in rinsing with water.

The invention will now be illustrated more fully with the aid of the examples which follow, which should not be considered as limiting it to the embodiments described. In the text which follows, AM means active material.

EXAMPLE 1

A haircare spray packaged in a pump-dispenser bottle, of the following composition, was prepared:

| | |
|---|---|
| grafted silicone polymer of formula (IV) of polymethyl/methylsiloxane structure containing 3-propylthio polyisobutyl methacrylate groups dissolved in a volatile cyclic silicone | 4 gAM |
| block copolymer of formula: $[[(CH_3)_2SiO]_x(CH_3)_2SiCH_2CH(CH_3)CH_2O—(C_2H_4O)_y—(C_3H_6O)_zCH_2CH(CH_3)CH_2]_n$ with $x = 9$ to 11, $y = 18$ to 25, $z = 28$ to 35 and n is such that the viscosity of a polymer solution at 10% in ethanol is about 50 mPa·s | 1 g |
| ethanol | qs 100 g |

EXAMPLE 2

Aerosol Hairstyling Spray

| | |
|---|---|
| grafted silicone polymer of formula (IV) of polymethyl/methylsiloxane structure containing 3-propylthio polymethacrylic acid groups 3-propylthio polymethy methacrylate groups | 5 g |
| block copolymer of formula: $[[(CH_3)_2SiO]_x(CH_3)_2SiCH_2CH(CH_3)CH_2O—(C_2H_4O)_y—(C_3H_6O)_zCH_2CH(CH_3)CH_2]_n$ with $x = 9$ to 11, $y = 18$ to 25, $z = 26$ to 35 and n is such that the viscosity of a polymer solution at 10% in ethanol is about 50 mPa·s | 1.25 g |
| vinyl acetate/crotonic acid/vinyl 4-tert-butylbenzoate copolymer (65/10/25) as described and prepared in patent FR 2,697,160 | 2.5 g |
| aminomethylpropanol for 100% neutralization of the grafted silicone polymer and the non-silicone copolymer qs | |
| ethanol | qs 100 g |
| Pressurization plan: | |
| Above composition: | 80 g |
| Ternary mixture of n-butane, isobutane and propane (23/55/22), sold under the name "Aerogaz 3.2 N" by the company Elf Aquitaine | 5 g |
| 1,1-Difluoroethane (Solkane 152 A from Solvay) | 15 g |

EXAMPLE 3

A haircare mousse of the following composition was prepared:

| | |
|---|---|
| grafted silicone polymer of formula (IV) of polymethyl/methylsiloxane structure containing 3-propylthio polymethacrylic acid groups and 3-propylthio polymethyl methacrylate groups | 3.3 g |

| | |
|---|---|
| aminomethylpropanol, 100% neutralization of the said silicone polymer | qs |
| block copolymer of formula: [[(CH$_3$)$_2$SiO]$_x$(CH$_3$)$_2$SiCH$_2$CH(CH$_3$)CH$_2$O—(C$_2$H$_4$O)$_y$—(C$_3$H$_6$O)$_z$CH$_2$CH(CH$_3$)CH$_2$]$_n$ with x = 9 to 11, y = 18 to 25, z = 28 to 35 and n is such that the viscosity of a polymer solution at 10% in ethanol is about 50 mPa · s | 2.2 g |
| ethanol | 9.7 g |
| demineralized water | qs 100 g |
| Pressurization schema: | |
| Above composition: | 90 g |
| Ternary mixture of n-butane, isobutane and propane (23/55/22), sold under the name "Aerogaz 3.2 N" by the company Elf Aquitaine | 10 g |

EXAMPLE 4

A styling gel of the following composition was prepared:

| | |
|---|---|
| copolymer consisting of: | 8 g | a) 60% by weight of tert-butyl acrylate;
b) 20% by weight of acrylic acid;
c) 20% by weight of silicone macromer of formula:

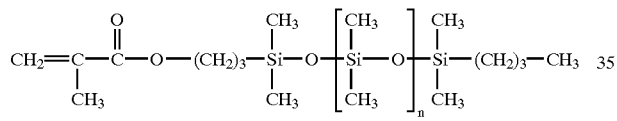

with n being a number chosen such that the number-average molecular weight of the polymer is approximately 9000–12,000; the weight percentages being calculated relative to the total weight of the monomers,

| | |
|---|---|
| aminomethylpropanol, 100% neutralization of the said silicone polymer qs | |
| block copolymer of formula: [[(CH$_3$)$_2$SiO]$_x$(CH$_3$)$_2$SiCH$_2$CH(CH$_3$)CH$_2$O—(C$_2$H$_4$O)$_y$—(C$_3$H$_6$O)$_z$CH$_2$CH(CH$_3$)CH$_2$]$_n$ with x = 9 to 11, y = 18 to 25, z = 28 to 35 and n is such that the viscosity of a polymer solution at 10% in ethanol is about 50 mPa · s | 2 g |
| demineralized water | 40 g |
| ethanol | qs 100 g |

EXAMPLE 5

A shampoo of the following composition was prepared:

| | |
|---|---|
| grafted silicone polymer of formula (IV) of polymethyl/methylsiloxane structure containing 3-propylthio polymethacrylic acid groups and 3-propylthio polymethyl methacrylate groups | 2 g |
| sodium lauryl (C$_{12}$/C$_{14}$ 70/30) ether sulphate oxyethylenated with 2.2 mol of ethylene oxide as an aqueous solution containing 28% AM, sold under the name Empicol ESB 3/FL by the company Albright and Wilson | 12 g AM |
| cocoylbetaine in aqueous solution at 28% AM | 2 g AM |
| block copolymer of formula: [[(CH$_3$)$_2$SiO]$_x$(CH$_3$)$_2$SiCH$_2$CH(CH$_3$)CH$_2$O—(C$_2$H$_4$O)$_y$—(C$_3$H$_6$O)$_z$CH$_2$CH(CH$_3$)CH$_2$]$_n$ with x = 9 to 11, y = 18 to 25, z = 28 to 35 and n is such that the viscosity of a polymer solution at 10% in ethanol is about 50 mPa · s | 0.5 g |
| fragrance, sequestering agent, preserving agent | |
| water | qs 100 g |

The ph is adjusted to 5.8 by addition of hydrochloric acid.

EXAMPLE 6

A rinse-out conditioner of the following composition was prepared:

| | |
|---|---|
| mixture (80/20 by weight) of cetylstearyl alcohol and of cetylstearyl alcohol oxyethylenated with 33 mol of ethylene oxide | 2 g |
| grafted silicone polymer of formula (IV) of polymethyl/methylsiloxane structure containing 3-propylthio polyisobutyl methacrylate groups, dissolved in a volatile cyclic silicone | 2 g |
| behenyltrimethylammonium chloride containing 88% AM in a water/isopropanol mixture (15/85), sold under the name Catinal DC 80 (Toho) | 2 g AM |
| block copolymer of formula: [[(CH$_3$)$_2$SiO]$_x$(CH$_3$)$_2$SiCH$_2$CH(CH$_3$)CH$_2$O—(C$_2$H$_4$O)$_y$—(C$_3$H$_6$O)$_z$CH$_2$CH(CH$_3$)CH$_2$]$_n$ with x = 9 to 11, y = 18 to 25, z = 28 to 35 and n is such that the viscosity of a polymer solution at 10% in ethanol is about 50 mPa · s | 0.5 g |
| fragrance, preserving agent | |
| water | qs 100 g |

The pH is adjusted to 5 by addition of 5 hydrochloric acid.

Comparative Examples

I Fixing Power

The fixing power obtained by the three formulations A, B and C below were studied and compared:

| COMPOSITION A (prior art): | |
|---|---|
| grafted silicone polymer P$_1$ of formula (IV) of polymethyl/methylsiloxane structure containing 3-propylthio polymethacrylic acid groups and 3-propylthio polymethyl methacrylate groups (aqueous 10% solution) | 5 g AM |
| tripropylene glycol monomethyl ether (plasticizer) | 0.5 g |
| aminomethylpropanol, 100% neutralization of the grafted silicone polymer qs | |
| 98.5% ethanol | qs 100 g |

-continued

COMPOSITION B (invention):

| | |
|---|---|
| grafted silicone polymer $P_1$ of formula (IV) of polymethyl/methylsiloxane structure containing 3-propylthio polymethacrylic acid groups and 3-propylthio polymethyl methacrylate groups (10% solution) | 5 g AM |
| block copolymer ($P_2$) of formula: $[[(CH_3)_2SiO]_x(CH_3)_2SiCH_2CH(CH_3)CH_2O—(C_2H_4O)_y—(C_3H_6O)_zCH_2CH(CH_3)CH_2]_n$ with x = 9 to 11, y = 18 to 25, z = 28 to 35 and n is such that the viscosity of a polymer solution at 10% in ethanol is about 50 mPa · s | 1 g |
| tripropylene glycol monomethyl ether (plasticizer) | 0.5 g |
| aminomethylpropanol, 100% neutralization of the grafted silicone polymer qs | |
| 98.5% ethanol | qs 100 g |

COMPOSITION C (prior art):

| | |
|---|---|
| grafted silicone polymer $P_1$ of formula (IV) of polymethyl/methylsiloxane structure containing 3-propylthio polymethacrylic acid groups and 3-propylthio polymethyl methacrylate groups (aqueous 10% solution) | 5 g AM |
| aminomethylpropanol, 100% neutralization of the grafted silicone polymer qs | |
| tripropylene glycol monomethyl ether (plasticizer) | 0.5 g |
| dimethicone copolyol sold under the name Mirasil DMCO by the company Rhône-Poulenc | 1 g |
| 98.5% ethanol | qs 100 g |

Procedure

A test for measurement of the strength of the bonds formed between hairs by a hair lacquer is carried out according to the principles of the method described in the article by R. Randall Wickett, John A. Sramek and Cynthia M. Trobaugh in J. Soc. Cosmet. Chem. 43, 169–178 (May/June 1992).

A single strand of hair is taken for each formulation tested. The strand of hair is made into a simple loop having a diameter of approximately 2 cm, using a cylindrical support. The hair thus looped is soaked in the formulation and is left to dry under a conditioned atmosphere (20° C. and 50% humidity). The loop fixed with formulation A, B or C is cut. 2 half-strands of hair linked together by a fixing point are thus obtained.

The ends, located on either side of the fixing point, are fixed in each of the two jaws of an Instron® type machine which measures the tensile force in Newtons exerted on the half-strands of hair.

The average force (average of ten tests) $F_A$, $F_B$ and $F_C$ (specific to composition A, B or C) required to break the fixing point joining the two half-strands of hair and formed by the formulation A, B or C is measured.

The enhancement afforded by the combination of the grafted silicone polymer $P_1$ and the copolymer $P_2$ relative to the polymer $P_1$ (composition A) used alone or relative to the combination of $P_1$ and a polyoxyalkylenated silicone (composition C) is determined by calculating the relative variation in the breaking force measured, expressed as a percentage, according to the following formula:

$(F_B-F_A/F_A) \times 100$ or $(F_B-F_C/F_C) \times 100$

The results are given in the table below:

| FORMULATION TESTED | AVERAGE BREAKING FORCE EXPRESSED IN NEWTONS | ENHANCEMENT OF THE FIXING POWER IN % |
|---|---|---|
| B (Invention) | 0.24 | — |
| A (Comparative) | 0.09 | 166% |
| C (Comparative) | 0.10 | 140% |

The fixing power of the composition according to the invention is markedly superior to that of the compositions of the prior art.

What is claimed is:

1. A cosmetic or dermatological composition comprising, in a cosmetically or dermatologically acceptable medium,
    (a) at least one grafted silicone polymer comprising a polysiloxane portion and a non-silicone organic chain portion, wherein one portion constitutes the main chain of said at least one grafted silicone polymer and the other portion is grafted onto said main chain, and
    (b) at least one copolymer comprising repeating units of a linear polysiloxane/polyoxyalkylene block, wherein said (a) differs from said (b).

2. A cosmetic or dermatological composition according to claim 1, wherein said at least one grafted silicone polymer is a polymer having a non-silicone organic skeleton grafted with at least one monomer containing a polysiloxane or a polymer having a polysiloxane skeleton grafted with at least one non-silicone organic monomer.

3. A cosmetic or dermatological composition according to claim 1, wherein said at least one grafted silicone polymer contains a non-silicone organic skeleton comprising an organic main chain formed from at least one non-silicone organic monomer on which is grafted, inside said chain and optionally on at least one end of said chain, at least one polysiloxane macromer.

4. A cosmetic or dermatological composition according to claim 3, wherein said at least one non-silicone organic monomer is a monomer containing ethylenic unsaturation which is polymerizable via a radical route, a monomer which is polymerizable by polycondensation or a monomer which involves ring opening.

5. A cosmetic or dermatological composition according to claim 1, wherein said composition comprises at least one silicone grafted copolymer comprising:
    a) up to 98% by weight of at least one lipophilic monomer (A) of low polarity containing ethylenic unsaturation of low polarity, which is polymerizable via a radical route;
    b) up to 98% by weight of at least one polar hydrophilic monomer (B) containing ethylenic unsaturation, which is copolymerizable with said(A) monomer(s);
    c) from 0.01 to 50% by weight of at least one polysiloxane macromer (C) of formula:

$$X(Y)_n Si(R)_{3-m} Z_m \qquad (I)$$

in which:
    X denotes a vinyl group which is copolymerizable with said monomers (A) and (B);
    Y denotes a divalent bonding group;
    R denotes a hydrogen, a $C_1$–$C_6$ alkyl or alkoxy or a $C_8$–$C_{12}$ aryl;
    Z denotes a monovalent polysiloxane unit having a number-average molecular weight of at least 500;
    n is 0 or 1; and m is an integer ranging from 1 to 3;
wherein the percentages are calculated relative to the total weight of monomers (A), (B) and (C), and wherein the sum of a) and b) cannot constitute 0% by weight relative to the total weight of the monomers.

6. A cosmetic or dermatological composition according to claim 5, wherein said at least one lipophilic monomer (A) is an acrylic and methacrylic acid ester of a $C_1$–$C_{18}$ alcohol; styrene; a polystyrene macromer; vinyl acetate; vinyl propionate; α-methylstyrene; tert-butylstyrene; butadiene; cyclohexadiene; ethylene; propylene; vinyltoluene; an acrylic and methacrylic acid ester of a 1,1-dihydroperfluoroalkanol and of a homologue thereof; an acrylic and methacrylic acid ester of a ω-hydridofluoroalkanol; an acrylic and methacrylic acid ester of a fluoroalkylsulphoamido alcohol; an acrylic and methacrylic acid ester of a fluoroalkyl alcohol; or an acrylic and methacrylic acid ester of a fluoroether alcohol.

7. A cosmetic or dermatological composition according to claim 6, wherein said at least one lipophilic monomer (A) is n-butyl methacrylate, isobutyl methacrylate, tert-butyl acrylate, tert-butyl methacrylate, 2-ethylhexyl methacrylate, methyl methacrylate, 2-(Nbutylperfluorooctenesulphonamido)ethyl acrylate, or 2-(N-methylperfluorooctanesulphonamido)ethyl acrylate.

8. A cosmetic or dermatological composition according to claim 5, wherein said at least one polar hydrophilic monomer (B) is acrylic acid, methacrylic acid, N,N-dimethylacrylamide, dimethylaminoethyl methacrylate, quaternized dimethylaminoethyl methacrylate, (meth) acrylamide, N-t-butylacrylamide, maleic acid, maleic anhydride and a demiester thereof, a hydroxyalkyl (meth) acrylate, diallyidimethylammonium chloride, vinylpyrrolidone, a vinyl ester, a maleimide, vinylpyridine, vinylimidazole, a heterocyclic vinyl polar compound, styrene sulphonate, allyl alcohol, vinyl alcohol and vinyl caprolactam.

9. A cosmetic or dermatological composition according to claim 8, wherein said at least one polar hydrophilic monomer (B) is acrylic acid, N,N-dimethylacrylamide, dimethylaminoethyl methacrylate, quaternized dimethylaminoethyl methacrylate or vinylpyrrolidone.

10. A cosmetic or dermatological composition according to claim 5, wherein said at least one polysiloxane macromer (C) corresponds to the formula (II):

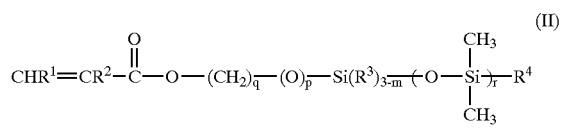

in which:
R$^1$ is hydrogen or —COOH;
R$^2$ is hydrogen, methyl or —CH$_2$COOH;
R$^3$ is $C_1$–$C_6$ alkyl, alkoxy, or alkylamino, $C_6$–$C_{12}$ aryl or hydroxyl;
R$^4$ is $C_1$–$C_6$ alkyl, alkoxy or alkylamino, $C_6$–$C_{12}$ aryl or hydroxyl;
q is an integer from 2 to 6;
p is 0 or 1;
r is an integer from 5 to 700;
m is an integer from 1 to 3.

11. A cosmetic or dermatological composition according to claim 10, with at least one of the following characteristics:

R$^1$ is hydrogen;
R$^2$ is methyl;
R$^3$ is methyl;
R$^4$ is methyl;
q is 3; and
m is 1.

12. A cosmetic or dermatological composition according to claim 10, wherein said at least one polysiloxane macromer (C) is selected from compounds corresponding to the following formula:

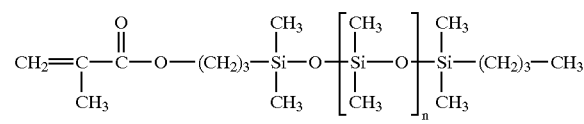

in which
n is an integer ranging from 5 to 700.

13. A cosmetic or dermatological composition according to claim 1, wherein said at least one grafted silicone polymer contains at least one copolymer which can be obtained by radical polymerization of a monomer mixture comprising:
a) 60% by weight of tertbutyl acrylate;
b) 20% by weight of acrylic acid;
c) 20% by weight of silicone macromer of formula:

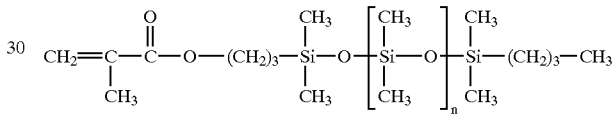

in which:
n is an integer ranging from 5 to 700;
wherein the weight percentages are calculated relative to the total weight of said monomer mixture.

14. A cosmetic or dermatological composition according to claim 1, wherein said at least one grafted silicone polymer contains at least one copolymer which can be obtained by radical polymerization of a monomer mixture comprising:
a) 50% by weight of tert-butyl acrylate;
b) 20% by weight of silicone macromer of formula:

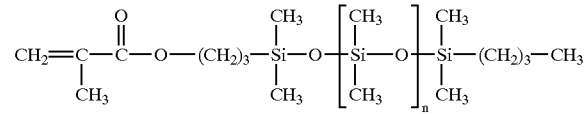

in which:
n is an integer ranging from 5 to 700;
wherein the weight percentages being calculated relative to the total weight of said monomer mixture.

15. A cosmetic or dermatological composition according to claim 2, wherein said at least one grafted silicone polymer contains a non-silicone organic skeleton grafted with at least one monomer containing a polysiloxane and has a number-average molecular weight ranging from 10,000 to 2,000,000 and a glass transition temperature Tg or a crystalline melting point Tm of at least −20° C.

16. A cosmetic or dermatological composition according to claim 1, wherein said at least one grafted silicone polymer contains a non-silicone organic skeleton grafted with at least one monomer containing a polysiloxane, wherein said at least one grafted silicone polymer is obtained by reactive extrusion of a polysiloxane macromer having a terminal reactive function, with a polyolefin polymer containing reactive groups which can react with the reactive terminal function of said polysiloxane macromer to form a covalent bond resulting in a grafting of the silicone to said polyolefin polymer, said polyolefin polymer forming the skeleton of said polymers.

17. A cosmetic or dermatological composition according to claim 16, wherein said polyolefin polymer is a polyethylene or a polymer of ethylene-derived monomers containing reactive functions which can react with the terminal function of said polysiloxane macromer.

18. A cosmetic or dermatological composition according to claim 17, wherein said polyolefin polymer is a copolymer of ethylene and/or of an ethylene derivative and of a monomer selected from a monomer containing a carboxylic function; a monomer containing an acid anhydride function; a monomer containing an acid chloride function; a monomer containing an ester function; or a monomer containing an isocyanate function.

19. A cosmetic or dermatological composition according to claim 16, wherein said polysiloxane macromer is a polysiloxane containing a functionalized group, located at the end of the polysiloxane chain or close to the end of said chain, said functionalized group being alcohols, thiols, epoxy groups, primary amines or secondary amines.

20. A cosmetic or dermatological composition according to claim 19, wherein said polysiloxane macromer is a polysiloxane corresponding to the formula (III):

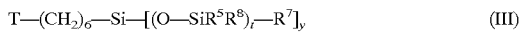

(III)

in which:
T is selected from $NH_2$, NHR', an epoxy, OH, and SH functions;
$R^5$, $R^6$, $R^7$ and R' each independenty denotes a $C_1$–$C_6$ alkyl, phenyl, benzyl, $C_6$–$C_{12}$ alkylphenyl or hydrogen;
s is a number ranging from 2 to 100;
t is a number ranging from 0 to 1000; and
y is a number ranging from 1 to 3.

21. A cosmetic or dermatological composition according to claim 2, wherein said composition comprises at least one grafted silicone polymer containing a polysiloxane main chain grafted with at least one non-silicone organic monomer, wherein on said polysiloxane main chain is grafted, inside said main chain as well as, optionally, on at least one of its ends, said at least one non-silicone organic monomer.

22. A cosmetic or dermatological composition according to claim 21, wherein said at least one grafted silicone polymer is obtained by radical copolymerization between:
at least one non-silicone organic monomer having ethylenic unsaturation selected from anionic and hydrophobic monomers, and
at least one polysiloxane having in its chain at least one functional group capable of reacting with said ethylenic unsaturation of said at least one non-silicone organic monomer.

23. A cosmetic or dermatological composition according to claim 21, wherein said anionic organic monomer is linear or branched, unsaturated carboxylic acids optionally partially or totally neutralized in the form of a salt.

24. A cosmetic or dermatological composition according to claim 23, wherein said anionic organic monomer is acrylic acid, methacrylic acid, maleic acid, maleic anhydride, itaconic acid, fumaric acid, crotonic acid, an alkali-metal salt of the above acids, an alkaline-earth metal salt of the above acids or an ammonium salt of the above acids.

25. A cosmetic or dermatological composition according to claim 22, wherein said hydrophobic organic monomer is an acrylic acid ester of alkanol or a methacrylic acid ester of alkanol.

26. A cosmetic or dermatological composition according to claim 25, wherein said alkanol is $C_1$–$C_{12}$.

27. A cosmetic or dermatological composition according to claim 26, wherein said alkanol is $C_1$–$C_{12}$.

28. A cosmetic or dermatological composition according to claim 22, wherein said hydrophobic organic monomer is isooctyl (meth)acrylate, isononyl (meth)acrylate, 2ethyl-hexyl (meth)acrylate, lauryl (meth)acrylate, isopentyl (meth)acrylate, n-butyl (meth)acrylate, isobutyl (meth) acrylate, methyl (moth)acrylate, tert-butyl (meth)acrylate, tridecyl (meth)acrylate or stearyl (meth)acrylate.

29. A cosmetic or dermatological composition according to claim 21, wherein said at least one grafted silicone polymer comprises, on the main silicone chain, at least one non-silicone organic group of anionic nature obtained by the radical (homo)polymerization of at least one non-silicone anionic monomer of unsaturated carboxylic acid type, which is partially or totally neutralized in the form of a salt.

30. A cosmetic or dermatological composition according to claim 29, wherein said at least one grafted silicone polymer is selected from silicone polymers containing in their structure the unit of formula (IV):

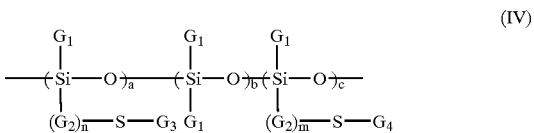

(IV)

in which:
the radicals $G_1$ each independently represent hydrogen or a $C_1$–$C_{10}$ alkyl radical or a phenyl radical;
the radicals $G_2$ each independently represent a divalent $C_1$–$C_{10}$ alkylene group;
$G_3$ represents a polymer residue resulting from the (homo)polymerization of at least one anionic monomer containing ethylenic unsaturation;
$G_4$ represents a polymer residue resulting from the (homo)polymerization of at least one hydrophobic monomer containing ethylenic unsaturation;
m and n are equal to 0 or 1;
a is an integer ranging from 0 to 50;
b is an integer ranging from 10 to 350,
c is an integer ranging from 0 to 50;
with the proviso that one of a and c is not 0.

31. A cosmetic or dermatological composition according to claim 30, wherein said unit of formula (IV) has at least one of the following characteristics:
the radicals $G_1$ each denote a $C_1$–$C_{10}$ alkyl radical;
n is non-zero and the radicals $G_2$ each represent a divalent $C_1$–$C_3$ radical;
$G_3$ represents a polymeric residue resulting from the (homo)polymerization of at least one carboxylic acid monomer containing ethylenic unsaturation; and
$G_4$ represents a polymeric residue resulting from the (homo)polymerization of at least one $C_1$–$C_{10}$ alkyl (meth)acrylate monomer.

32. A cosmetic or dermatological composition according to claim 30, wherein said unit of formula (IV) simultaneously has the following characteristics:
the radicals $G_1$ denote a methyl radical;
n is 1 and the radicals $G_2$ represent a propylene radical;
$G_3$ represents a polymeric residue resulting from the (homo)polymerization of at least one acrylic acid and/or methacrylic acid;
$G_4$ represents a polymeric residue resulting from the (homo)polymerization of at least one isobutyl or methyl (meth)acrylate monomer.

33. A cosmetic or dermatological composition according to claim 1, wherein the number-average molecular mass of said at least one grafted silicone polymer ranges from 10,000 to 1,000,000.

34. A cosmetic or dermatological composition according to claim 33, wherein said number-average molecular mass of said at least one grafted silicone polymer ranges from 10,000 to 100,000.

35. A cosmetic or dermatological composition according to claim 1, wherein said at least one grafted silicone polymer is present in a concentration ranging from 0.01 to 20% by weight relative to the total weight of said composition.

36. A cosmetic or dermatological composition according to claim 35, wherein said at least one grafted silicone polymer is present in a concentration ranging from 0.1 to 15% by weight relative to the total weight of said composition.

37. A cosmetic or dermatological composition according to claim 36, wherein said at least one grafted silicone polymer is present in a concentration ranging from 0.5 to 10% by weight relative to the total weight of said composition.

38. A cosmetic or dermatological composition according to claim 1, wherein said linear polysiloxane/polyoxyalkylene block corresponds to the formula:

in which:
R and R' each independently represents a monovalent hydrocarbon radical containing no aliphatic unsaturation,
n is an integer ranging from 2 to 4,
a is an integer greater than or equal to 5,
b is an integer greater than or equal to 4,
c is an integer greater than or equal to 4,
Y represents a divelent organic group which is linked to the adjacent silicon atom via a carbon-silicon bond and to a polyoxyalkylene block via an oxygen atom,
the average molecular weight of each polysiloxane block ranges from 400 to 10,000, and the average molecular weight of each polyoxyalkylene block ranges from 300 to 10,000,
wherein said polysiloxane blocks represent from 10% to 95% of the weight of said at least one copolymer, and
the average molecular weight of said at least one copolymer is at least 3000.

39. A cosmetic or dermatological composition according to claim 38, wherein a ranges from 5 to 200.

40. A cosmetic or dermatological composition according to claim 39, wherein a ranges from 5 to 100.

41. A cosmetic or dermatological composition according to claim 38, wherein b ranges from 4 to 200.

42. A cosmetic or dermatological composition according to claim 41, wherein b ranges from 5 to 100.

43. A cosmetic or dermatological composition according to claim 38, wherein c ranges from 4 to 1000.

44. A cosmetic or dermatological composition according to claim 43, wherein c ranges from 5 to 300.

45. A cosmetic or dermatological composition according to claim 38, wherein R and R' are independently methyl, ethyl, propyl, butyl, pentyl, hexyl, octyl, decyl, dodecyl, phenyl, naphthyl, benzyl, phenylethyl, tolyl, xylyl or cyclohexyl radicals.

46. A cosmetic or dermatological composition according to claim 38, wherein Y is selected from —R"—, —R"—CO—, —R"—NHCO—, R"—NH—CONH— R'"NHCO and R"—OCONH—R'"—NHCO—,
in which:
R" represents an ethylene, propylene or butylene radical and
R" represents a —$C_6H_4$—, —$C_6H_4$—$C_6H_4$—, —$C_6H_4$—$CH_2$—$C_6H_4$ or —$C_6H_4$—$CH(CH_3)_2$— $C_6H_4$-group.

47. A cosmetic or dermatological composition according to claim 1, wherein said at least one copolymer comprising repeating units of a linear polysiloxane/polyoxyalkylene block is selected from those of formula (VI):

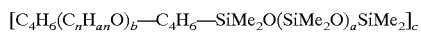

in which:
Me denotes methyl,
n is an integer ranging from 2 to 4,
a and b are integers greater than or equal to 4 and
c is a number greater then or equal to 4.

48. A cosmetic or dermatological composition according to claim 47, wherein said linear polysiloxane/polyoxyalkylene block corresponds to the formula (Vll):

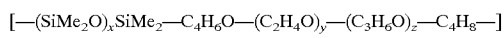

in which:
x is a number ranging from 5 to 15,
y is a number ranging from 15 to 30, and
z is a number ranging from 20 to 40.

49. A cosmetic or dermatological composition according to claim 1, wherein said at least one copolymer comprising repeating units of a linear polysiloxane/polyoxyalkylene block is:
[[($CH_3$)$_2$SiO]$_{41}$($CH_3$)$_2$SiCH$_2$CH($CH_3$)CH$_2$—O($C_2$H$_4$O)$_{16}$—($C_3$H$_6$O)$_{33}$CH$_2$CH($CH_3$)CH$_2$]$_{16.1}$;
[[($CH_3$)$_2$SiO]$_{31}$($CH_3$)$_2$SiCH$_2$CH($CH_3$)CH$_2$—O($C_2$H$_4$O)$_{20}$—($C_3$H$_6$O)29CH$_2$CH($CH_3$)CH$_2$]$_{13.3}$;
[[($CH_3$)$_2$SiO$_9$($CH_3$)$_2$SiCH$_2$CH($CH_3$)CH$_2$—O($C_2$H$_4$O)$_{20}$—($C_3$H$_6$O)29CH$_2$CH($CH_3$)CH$_2$]$_{26.3}$;
[[($CH_3$)$_2$SiO]$_{16}$($CH_3$)$_2$SiCH$_2$CH($CH_3$)CH$_2$—O($C_2$H$_4$O)$_{16}$—($C_3$H$_6$O)$_{20}$CH$_2$CH($CH_3$)CH$_2$]$_{21.5}$; or
[[($CH_3$)$_2$SiO]$_9$($CH_3$)$_2$SiCH$_2$CH($CH_3$)CH$_2$—($C_2$H$_4$O)$_5$—CH$_2$CH($CH_3$)CH$_2$]$_{4.6}$.

50. A cosmetic or dermatological composition according to claim 1, wherein said at least one copolymer is present in a concentration ranging from 0.01 to 20% by weight relative to the total weight of said composition.

51. A cosmetic or dermatological composition according to claim 50, wherein said at least one copolymer is present in a concentration ranging from 0.1 to 15% by weight relative to the total weight of said composition.

52. A cosmetic or dermatological composition according to claim 51, wherein said at least one copolymer is present in a concentration ranging from 0.5 to 10% by weight relative to the total weight of said composition.

53. A cosmetic or dermatological composition according to claim 1, wherein said composition further comprises at least one polymer in solubilized form or in dispersed form.

54. A cosmetic or dermatological composition according to claim 53, wherein said at least one polymer is a non-silicone anionic polymer or a non-silicone amphoteric polymer.

55. A cosmetic or dermatological composition according to claim 1, wherein said composition further comprises at least one additive which is a fatty chain-free thickener, a fatty acid ester, a fatty acid ester of glycerol, a silicone, a surfactant, a fragrance, a preserving agent, a sunscreen, a protein, a vitamin, a different polymer, a plant oil, an animal oil, a mineral oil, a synthetic oil or any suitable cosmetic additive.

56. A cosmetic or dermatological composition according to claim 1, wherein said cosmetically or dermatologically acceptable medium comprises water or a mixture of water and at least one cosmetically acceptable solvent.

57. A cosmetic or dermatological composition according to claim 56, wherein said at least one cosmetically acceptable solvent is a monoalcohol, a polyalcohol, a glycol ester or a fatty acid ester.

58. A cosmetic or dermatological composition according to claim 1, wherein said at least one grafted silicone polymer is dissolved in the cosmetically or dermatologically acceptable medium or is in the form of an aqueous dispersion of particles.

59. A cosmetic or dermatological composition according to claim 1, wherein said composition is a treatment composition for a keratin substance.

60. A cosmetic or dermatological composition according to claim 59, wherein said keratin substance is human hair.

61. A cosmetic or dermatological composition according to claim 1, wherein said composition is in the form of a gel, a milk, a cream, a thickened lotion or a foam.

62. A cosmetic or dermatological composition according to claim 1, wherein said composition is a styling product.

63. A cosmetic or dermatological composition according to claim 1, wherein said composition is a hair product to be applied before or after shampooing, dyeing, bleaching, permanent-waving or straightening the hair.

64. A cosmetic or dermatological composition according to claim 63, wherein said hair product is a shampoo, a rinse-out hair product or a leave-in hair product.

65. A cosmetic or dermatological composition according to claim 1, wherein said composition is packaged in the form of a vaporizer, a pump-dispenser bottle or in an aerosol container.

66. A non-therapeutic process for treating a keratin substance comprising applying a composition according to claim 1 to said keratin substance, and then optionally rinsing with water.

67. A non-therapeutic process according to claim 66, wherein said keratin substance is human hair.

* * * * *

UNITED STATES PATENT AND TRADEMARK OFFICE
CERTIFICATE OF CORRECTION

PATENT NO. : 6,432,418 B1
DATED : August 13, 2002
INVENTOR(S) : Claude Dubief et al.

It is certified that error appears in the above-identified patent and that said Letters Patent is hereby corrected as shown below:

Column 14,
Line 64, "$C_8$-$C_{12}$ aryl;" should read -- $C_6$-$C_{12}$ aryl; --.

Column 15,
Line 24, "2-(Nbutylperfluorooctenesulphonamido)ethyl" should read
-- 2-(N-butylperfluorooctanesulphonamido)ethyl --.
Line 33, "diallyidimethylammonium" should read -- diallyldimethylammonium --.

Column 17,
Line 31, "$T\text{-}(CH_2)_6\text{-}Si\text{-}[(O\text{-}SiR^5R^8)_t\text{-}R^7]_y$" should read -- $T\text{-}(CH_2)_s\text{-}Si\text{-}[(O\text{-}SiR^5R^6)_t\text{-}R^7]_y$ --.
Line 36, "independenty" should read -- independently --.
Line 62, "claim 21," should read -- claim 22, --.

Column 18,
Line 10, "$C_1$-$C_{12}$." should read -- $C_1$-$C_{18}$. --.
Lines 15-16, "2ethylhexyl" should read -- 2-ethylhexyl --.
Line 18, "methyl (moth)acrylate," should read -- methyl (meth)acrylate, --.

Column 19,
Line 38, "$9[Y(R_2SiO)_aR'_2SiYO][C_nH_{2n}O)_b])_c$" should read -- $([Y(R_2SiO)_aR'_2SiYO][(C_nH_{2n}O)_b])_c$ --.
Line 49, "divelent" should read -- divalent --.

Column 20,
Line 12, "R"-NH-CONH- R'"NHCO" should read -- R"-NH-CONH-R'"NHCO --.
Line 17, "R" represents" should read -- R'" represents --.
Line 18, "-$C_6H_4$-$CH(CH_3)_2$-$C_6H_4$-group" should read -- $C_6H_4$-$CH(CH_3)_2$-$C_6H_4$- group --.
Line 24, "$[C_4H_6(C_nH_{an}O)_b\text{-}C_4H_6\text{-}SiMe_2O(SiMe_2O)_aSiMe_2]_c$" should read
-- $C_4H_8(C_nH_{2n}O)_b\text{-}C_4H_8\text{-}SiMe_2O(SiMe_2O)_aSiMe_2]_c$ --.
Line 31, "greater then" should read -- greater than --.
Line 34, "formula (Vll):" should read -- formula (VII): --.
Line 36, "$[\text{-}(SiMe_2O)_xSiMe_2\text{-}C_4H_6O\text{-}(C_2H_4O)_y\text{-}(C_3H_6O)_z\text{-}C_4H_8\text{-}]$" should read
-- $[\text{-}(SiMe_2O)_xSiMe_2\text{-}C_4H_8O\text{-}(C_2H_4O)_y\text{-}(C_3H_6O)_z\text{-}C_4H_8\text{-}]$ --.
Lines 46-47, "$[[(CH_3)_2SiO]_{4l}(CH_3)_2SiCH_2CH(CH_3)CH_2\text{-}O(C_2H_4O)_{16}\text{-}(C_3H_6O)_{33}CH_2CH(CH_3)CH_2]_{16.1}$;" should read -- $[[(CH_3)_2SiO]_{4l}(CH_3)_2SiCH_2CH(CH_3)CH_2\text{-}O(C_2H_4O)_{18}\text{-}(C_3H_6O)_{33}CH_2CH(CH_3)CH_2]_{16.1}$; --.

UNITED STATES PATENT AND TRADEMARK OFFICE
CERTIFICATE OF CORRECTION

PATENT NO. : 6,432,418 B1
DATED : August 13, 2002
INVENTOR(S) : Claude Dubief et al.

It is certified that error appears in the above-identified patent and that said Letters Patent is hereby corrected as shown below:

Column 20 (cont'd),
Lines 48-49, "$[[(CH_3)_2SiO]_{31}(CH_3)_2SiCH_2CH(CH_3)CH_2-O(C_2H_4O)_{20}-(C_3H_6O)29CH_2CH(CH_3)CH_2]_{13.3}$;" should read -- $[[(CH_3)_2SiO]_{31}(CH_3)_2SiCH_2CH(CH_3)CH_2-O(C_2H_4O)_{20}-(C_3H_6O)_{29}CH_2CH(CH_3)CH_2]_{13.3}$; --.
Lines 50-51, "$[[(CH_3)_2SiO_9(CH_3)_2SiCH_2CH(CH_3)CH_2-O(C_2H_4O)_{20}-(C_3H_6O)29CH_2CH(CH_3)CH_2]_{26.3}$;" should read -- $[[(CH_3)_2SiO_9(CH_3)_2SiCH_2CH(CH_3)CH_2-O(C_2H_4O)_{20}-(C_3H_6O)_{29}CH_2CH(CH_3)CH_2]_{26.3}$; --.
Lines 52-53, "$[[(CH_3)_2SiO]_{16}(CH_3)_2SiCH_2CH(CH_3)CH_2-O(C_2H_4O)_{16}-(C_3H_6O)_{20}CH_2CH(CH_3)CH_2]_{21.5}$;" should read -- $[[(CH_3)_2SiO]_{16}(CH_3)_2SiCH_2CH(CH_3)CH_2-O(C_2H_4O)_{18}-(C_3H_6O)_{20}CH_2CH(CH_3)CH_2]_{21.5}$; --.
Lines 54-55, "$[[(CH_3)_2SiO]_9(CH_3)_2SiCH_2CH(CH_3)CH_2-(C_2H_4O)_5-CH_2CH(CH_3)CH_2]_{4.6}$." should read -- $[[(CH_3)_2SiO]_9(CH_3)_2SiCH_2CH(CH_3)CH_2-O(C_2H_4O)_5-CH_2CH(CH_3)CH_2]_{4.8}$. --.

Signed and Sealed this

Tenth Day of December, 2002

JAMES E. ROGAN
*Director of the United States Patent and Trademark Office*